(12) United States Patent
Shin et al.

(10) Patent No.: US 7,354,437 B2
(45) Date of Patent: Apr. 8, 2008

(54) ELECTRODE DEVICE FOR HIGH FREQUENCY THERMOTHERAPY

(75) Inventors: Kyong Min Shin, Seoul (KR); Hyo Keun Lim, Seoul (KR); Hyun Chul Rhim, Seoul (KR); Jeong Min Lee, Seoul (KR)

(73) Assignee: Taewoong Medical Co., Ltd., Kyunggi-do (KR)

( * ) Notice: Subject to any disclaimer, the term of this patent is extended or adjusted under 35 U.S.C. 154(b) by 106 days.

(21) Appl. No.: 10/546,050

(22) PCT Filed: Feb. 18, 2004

(86) PCT No.: PCT/KR2004/000330

§ 371 (c)(1), (2), (4) Date: Oct. 20, 2005

(87) PCT Pub. No.: WO2004/073792

PCT Pub. Date: Sep. 2, 2004

(65) Prior Publication Data

US 2006/0129144 A1    Jun. 15, 2006

(30) Foreign Application Priority Data

Feb. 19, 2003    (KR) .................. 10-2003-0010457

(51) Int. Cl.
*A61B 18/18* (2006.01)
(52) U.S. Cl. .................................. 606/41; 607/101
(58) Field of Classification Search .................. 606/41, 606/48–50; 607/101, 102
See application file for complete search history.

(56) References Cited

U.S. PATENT DOCUMENTS

| | | | | |
|---|---|---|---|---|
| 5,342,357 A | * | 8/1994 | Nardella | 606/40 |
| 5,403,311 A | * | 4/1995 | Abele et al. | 606/49 |
| 5,472,441 A | * | 12/1995 | Edwards et al. | 606/41 |
| 6,102,886 A | * | 8/2000 | Lundquist et al. | 604/22 |
| 6,238,393 B1 | * | 5/2001 | Mulier et al. | 606/41 |
| 6,315,777 B1 | * | 11/2001 | Comben | 606/41 |
| 6,379,349 B1 | * | 4/2002 | Muller et al. | 606/41 |
| 6,497,705 B2 | * | 12/2002 | Comben | 606/41 |
| 6,506,189 B1 | * | 1/2003 | Rittman et al. | 606/41 |
| 6,569,159 B1 | * | 5/2003 | Edwards et al. | 606/41 |
| 6,652,520 B2 | * | 11/2003 | Moorman et al. | 606/41 |
| 6,770,070 B1 | * | 8/2004 | Balbierz | 606/41 |
| 2002/0019628 A1 | * | 2/2002 | Comben | 606/34 |
| 2004/0143252 A1 | * | 7/2004 | Hurst | 606/41 |

FOREIGN PATENT DOCUMENTS

| | | |
|---|---|---|
| JP | 5-42166 | 2/1993 |
| JP | 7-265329 | 10/1995 |
| JP | 2000-287992 | 10/2000 |
| WO | WO 94/26186 | 11/1994 |

\* cited by examiner

*Primary Examiner*—Michael Peffley
*Assistant Examiner*—Victoria W Chen
(74) *Attorney, Agent, or Firm*—Jordan and Hamburg LLP

(57) ABSTRACT

The object of the present invention is to provide an electrode device for high frequency thermotherapy, including a main casing, an electrode needle, a first engaging part, and a guide unit coupled to the engaging part to be longitudinally moved relative to the electrode needle. The guide unit has a guide tube to receive therein the electrode needle to expose a tip of the electrode needle to the outside of an end of the guide tube. Thus, the exposed length of the tip of the electrode needle is varied according to a position that the guide unit is coupled to the engaging part. The electrode device may further include a three-way valve -provided between the main casing and the guide unit to supply a liquid medicine or water t a desired part of a patient body.

4 Claims, 10 Drawing Sheets

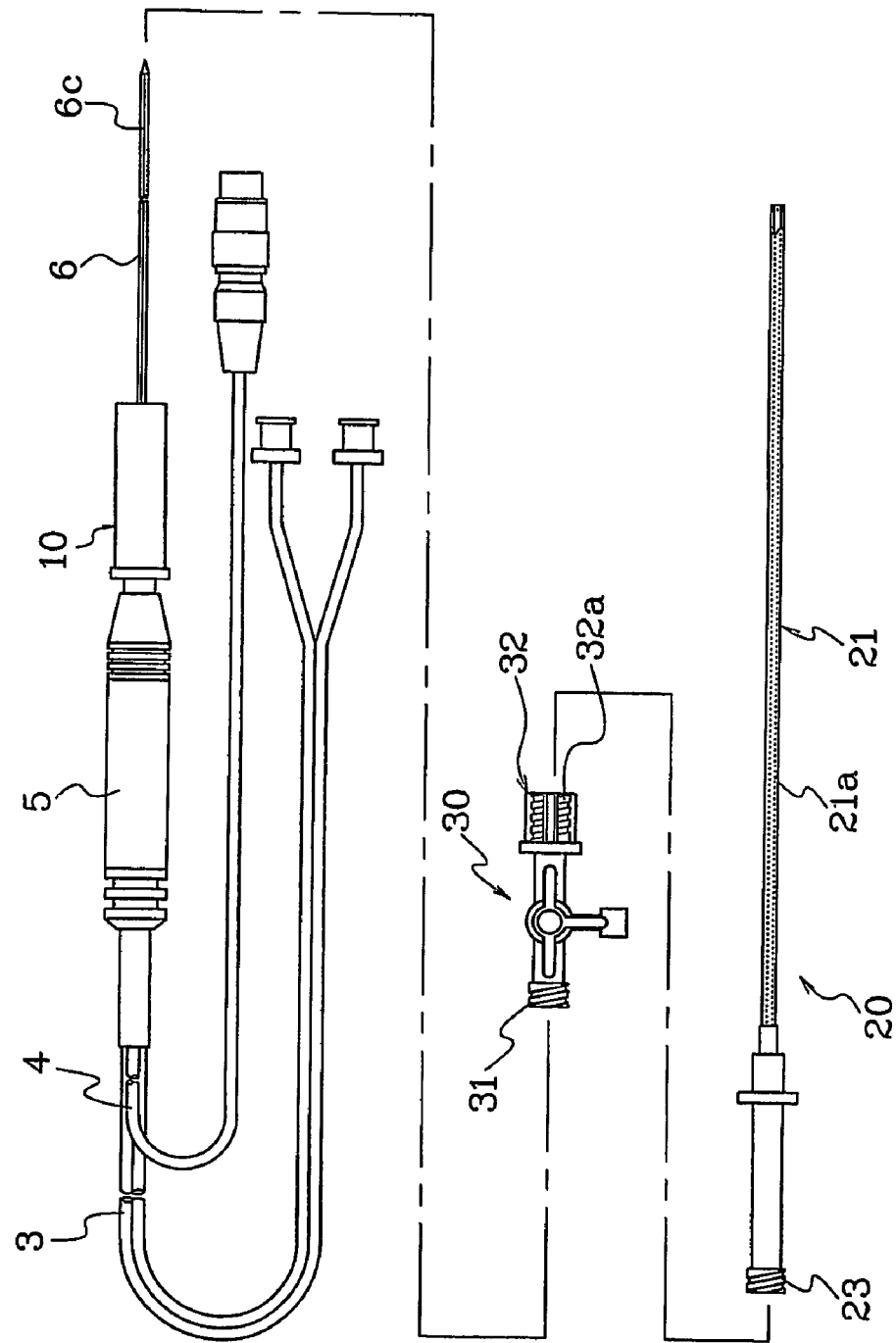

ELECTRODE DEVICE FOR HIGH FREQUENCY THERMOTHERAPY

TECHNICAL FIELD

The present invention relates, in general, to electrode devices for high frequency thermotherapy, which cauterize and necrotize lesions of patients, such as cancer tissues caused in the organs of the patients, using high-frequency heat and, more particularly, to an electrode device for high frequency thermotherapy, which controls a length of a conductive tip of an electrode needle, which is inserted into a lesion of a patient, or varies a conductive type of the electrode needle, or supplies water or liquid medicine to the lesion, thus controlling a range of cauterizing the lesion, efficiently cauterizing the lesion, and simplifying a thermotherapy operation.

BACKGROUND ART

Generally, a cancer is caused in an organ of a patient, such as a liver. The cancer is treated by a non-surgical operation or a surgical operation.

However, in case of the surgical operation, the skin of the patient must be cut over a large area prior to removal of a lesion from the patient body. Therefore, the surgical operation undesirably leaves a large and ugly scar on the skin of the patient and mars the appearance of the patient. Furthermore, the surgical operation undesirably forces the patient to spend a lengthy period of time for recovery.

Furthermore, when the cancer relapses in the organ of the patient, the surgical operation must be executed again. Thus, the repeated surgical operation undesirably forces the patient to undergo repeated severe pain, in addition to paying additional money. Furthermore, the repeated surgical operation is attended with danger.

To avoid the above-mentioned problems of the surgical operation, various types of non-surgical operations, such as a transarterial chemoembolization, a percutaneous ethanol injection, a general chemotherapy for cancer, a local thermotherapy and etc., have been used. The local thermotherapy is most effective in the above-mentioned non-surgical operations.

In the local thermotherapies, there are a high frequency thermotherapy, a microcauterization, a laser cauterization and etc. In the above-mentioned local thermotherapies, the high frequency thermotherapy has been most effectively used.

The high frequency thermotherapy is a therapy to cauterize and necrotize, for example, cancer tissues caused in the organ of a patient, such as the liver, using high frequency heat without cutting over the skin of the patient prior to the removal of the cancer tissues from the patient body.

As shown in FIG. 1, a conventional electrode device for the high frequency thermotherapy comprises a main casing 5, an electrode needle 6 which is coupled to a first end of the main casing 5, and an electrode cable 4 which is coupled to a second end of the main casing 5 to supply a high frequency wave to the electrode needle 6. The conventional electrode device further comprises a cooling tube 3 which is coupled to the second end of the main casing 5 to circulate cooling water to or from the electrode needle 6, thus preventing the electrode needle 6 from being damaged by the high frequency heat.

The electrode needle 6 typically includes a conductive needle part 6a which is defined at a predetermined part of a tip of the electrode needle 6, and an insulating needle part 6b which is defined at a remaining part of the electrode needle 6 except for the conductive needle part 6a.

At this time, preferably, a plurality of electrode needles 6, respectively having various conductive needle parts 6a of lengths different from each other, are prepared. Thus, during the thermotherapy operation, one of the various electrode needles 6 is selectively coupled to the main casing 5 to correspond to a size of the lesion of a patient. That is, the length of the conductive needle part 6a must be longer than a depth of a part of the lesion through that the tip of the electrode needle 6 passes. Therefore, the conductive needle part 6a cauterizes the lesion using the high frequency heat in a wider range than the lesion, thus firmly executing the operation.

The operation of the conventional electrode device for the high frequency thermotherapy is as follows. As shown in FIG. 2, the electrode needle 6, having the conductive needle part 6a corresponding to the size of the lesion 100 of the patient, is coupled to the main casing 5. Thereafter, the electrode cable 4 connects the electrode needle 6 to a high-frequency generator which is not shown. An electrode pad 2, which is in contact with a body of the patient, is connected to the high-frequency generator through an additional electrode cable.

Thereafter, the cooling tube 3, which is coupled to the main casing 5, is connected to a cooling pump (not shown) to circulate cooling water to or from the electrode needle 6.

In the above state, the electrode needle 6 is inserted into the lesion 100, such as the cancer tissues of the organ of the patient. Thereafter, the high frequency wave is supplied to the conductive needle part 6a of the electrode needle 6, except for the insulating needle part 6b, from the high-frequency generator. Thus, the lesion 100 is cauterized, and thus, necrotized by high frequency heat.

After the operation of cauterizing the lesion 100 is completed, the electrode needle 6 is removed from the body of the patient.

However, the conventional electrode device for the high frequency thermotherapy is problematic as follows.

First, because the length of the conductive needle part 6a of the electrode needle 6 is fixed, the conventional electrode device forces a user to purchase a plurality of electrode needles 6, of which the conductive needle parts 6a respectively have different lengths, and selectively use one of the plurality of electrode needles 6 according to a size of the lesion 100.

That is, the user must purchase the various electrode needles 6, of which the conductive needle parts 6a respectively have different lengths, for example, 1 cm, 2 cm, 3 cm and etc., prior to selectively using one of the various electrode needles 6. Therefore, the conventional electrode device forces the user to pay excessively, in addition to causing inconvenience for the user.

Second, in case that the thermotherapy operation is repeatedly executed several times on the lesion 100, or in case that the thermotherapy operation is executed while changing a plurality of electrode needles 6, the electrode needles 6 must be repeatedly inserted into and removed from a target portion of the patient body with the lesion 100. Therefore, the conventional electrode device causes severe pain and harm to the patient while the electrode needle(s) repeatedly prick(s) the target portion of the patient body.

Third, in the conventional electrode device including the electrode needle 6 of which the conductive needle part 6a has a predetermined fixed length, it is very difficult to control the range of cauterizing the lesion 100. That is, while the lesion 100 is cauterized by the electrode needle 6 with the conductive needle part 6a of the predetermined fixed length, the conventional electrode device does not have any means to control the range of cauterizing the lesion 100, except for controlling the power of the high frequency wave. Therefore, the electrode needle 6 must be repeatedly inserted into the lesion 100 through several parts of the patient body to cauterize the whole lesion 100

DISCLOSURE OF THE INVENTION

Accordingly, the present invention has been made keeping in mind the above-mentioned problems occurring in the prior art.

An object of the present invention is to provide an electrode device for high frequency thermotherapy, which has a structure capable of controlling a length of a predetermined part of a tip of an electrode needle, exposed from an end of a guide unit of the device to the outside, according to a size of a lesion, thus efficiently executing a thermotherapy operation, and being more convenient for a user.

Another object of the present invention is to provide an electrode device for high frequency thermotherapy, which supplies water or liquid medicine to the lesion to increase a range of radiating a high frequency wave, and thus, to increase a range of cauterizing the lesion, so that the number of operations for inserting the electrode needle to a desired part of a patient body is reduced, even when the lesion has a wide size.

A further object of the present invention is to provide an electrode device for high frequency thermotherapy, which has a guide tube inserted along with the electrode needle to the desired part of the patient body, so that only the electrode needle is inserted to or removed from the desired part through the inserted guide tube while the insertion of the guide tube is maintained, even when the thermotherapy operation is repeatedly executed, or the existing electrode needle is changed with another one, thus reducing pain of the patient and harm caused by repeated thermotherapy operations.

In order to accomplish the above object, the present invention provides an electrode device for high frequency thermotherapy, including a main casing, an electrode needle coupled to a first end of the main casing, a first engaging part provided on the first end of the main casing, and a guide unit coupled to the first engaging part of the main casing to be longitudinally moved relative to the electrode needle while the electrode needle is inserted in the guide unit. The guide unit has a guide tube to receive therein the electrode needle to expose a tip of the electrode needle to an outside of an end of the guide tube, with an insulating layer provided on an outer surface of the guide tube to insulate the guide tube from an outside of the guide tube. A length of the tip of the electrode needle, which is exposed from the end of the guide tube to the outside, is varied according to a position that the guide unit is coupled to the first engaging part of the main casing.

The electrode device may further include a three-way valve provided between the main casing and the guide unit, so that a liquid medicine or water is supplied from the three-way valve to a desired portion of a patient, thus increasing a range of cauterizing the desired portion of the patient by high frequency heat.

BRIEF DESCRIPTION OF THE DRAWINGS

The above and other objects, features and other advantages of the present invention will be more clearly understood from the following detailed description taken in conjunction with the accompanying drawings, in which:

FIG. 8 is an exploded view of an electrode device for high frequency thermotherapy, according to a third embodiment of the present invention;

BEST MODE FOR CARRYING OUT THE INVENTION

Figure 1:
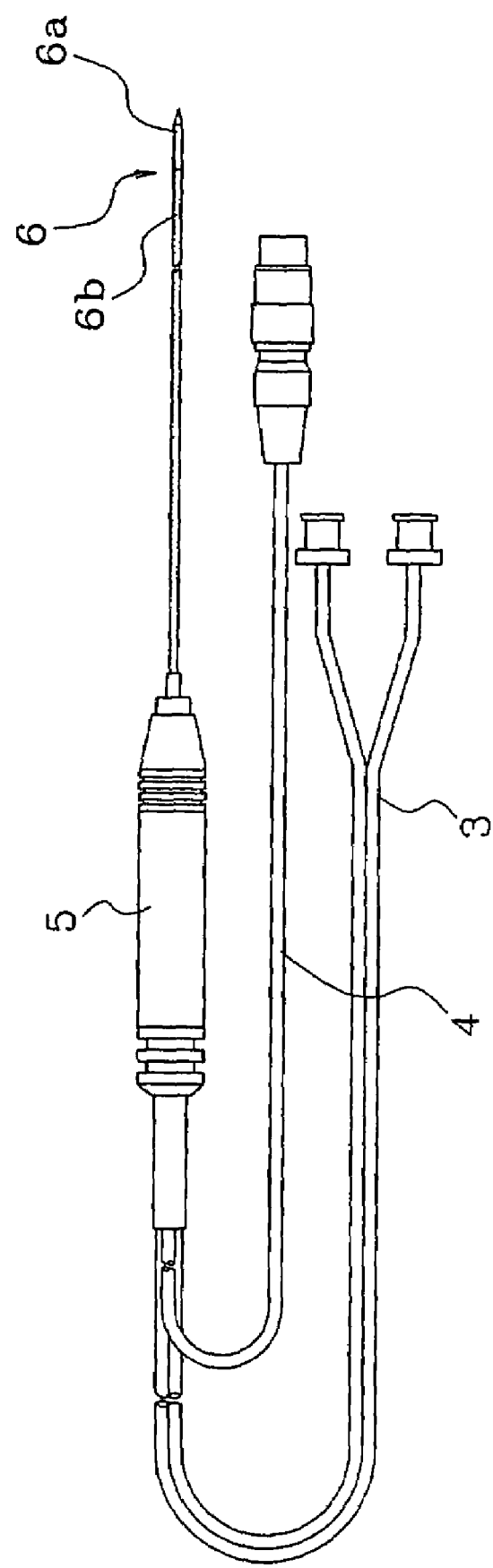
FIG. 1 is a front view of a conventional electrode device for high frequency thermotherapy.
Figure 2:
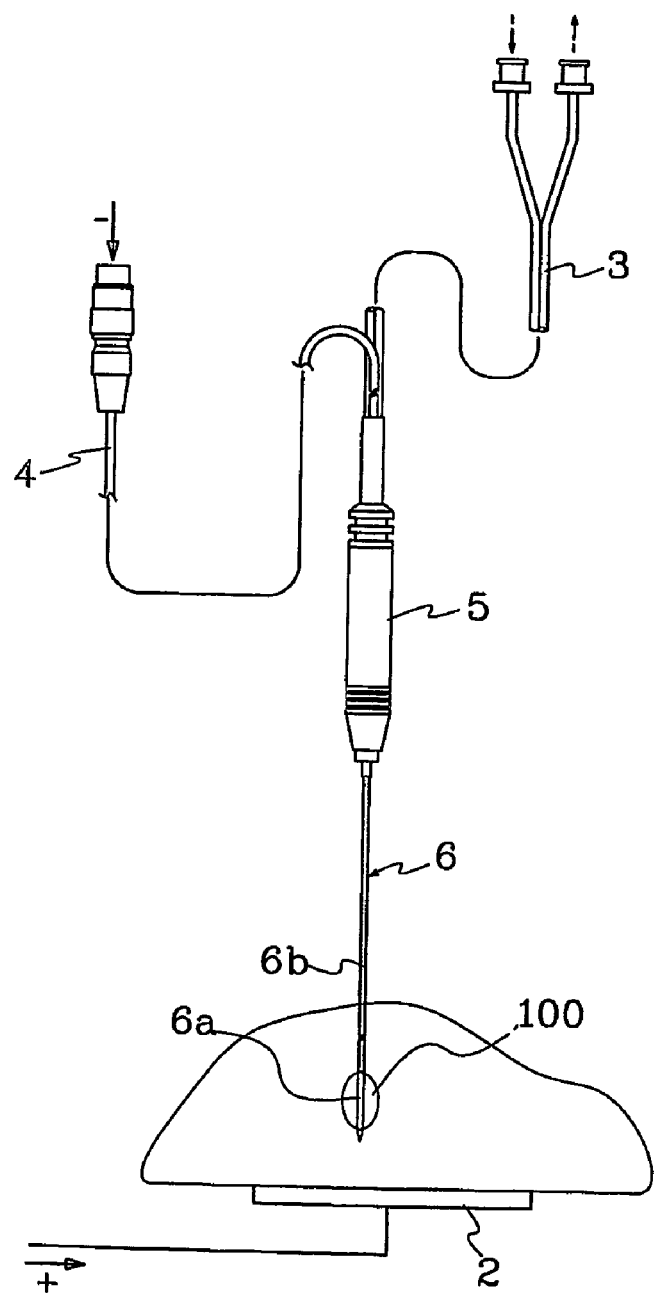
FIG. 2 is a view showing an operation of the electrode device of FIG. 1.

Reference should now be made to the drawings, in which the same reference numerals are used throughout the different drawings to designate the same or similar components.

Figure 3:
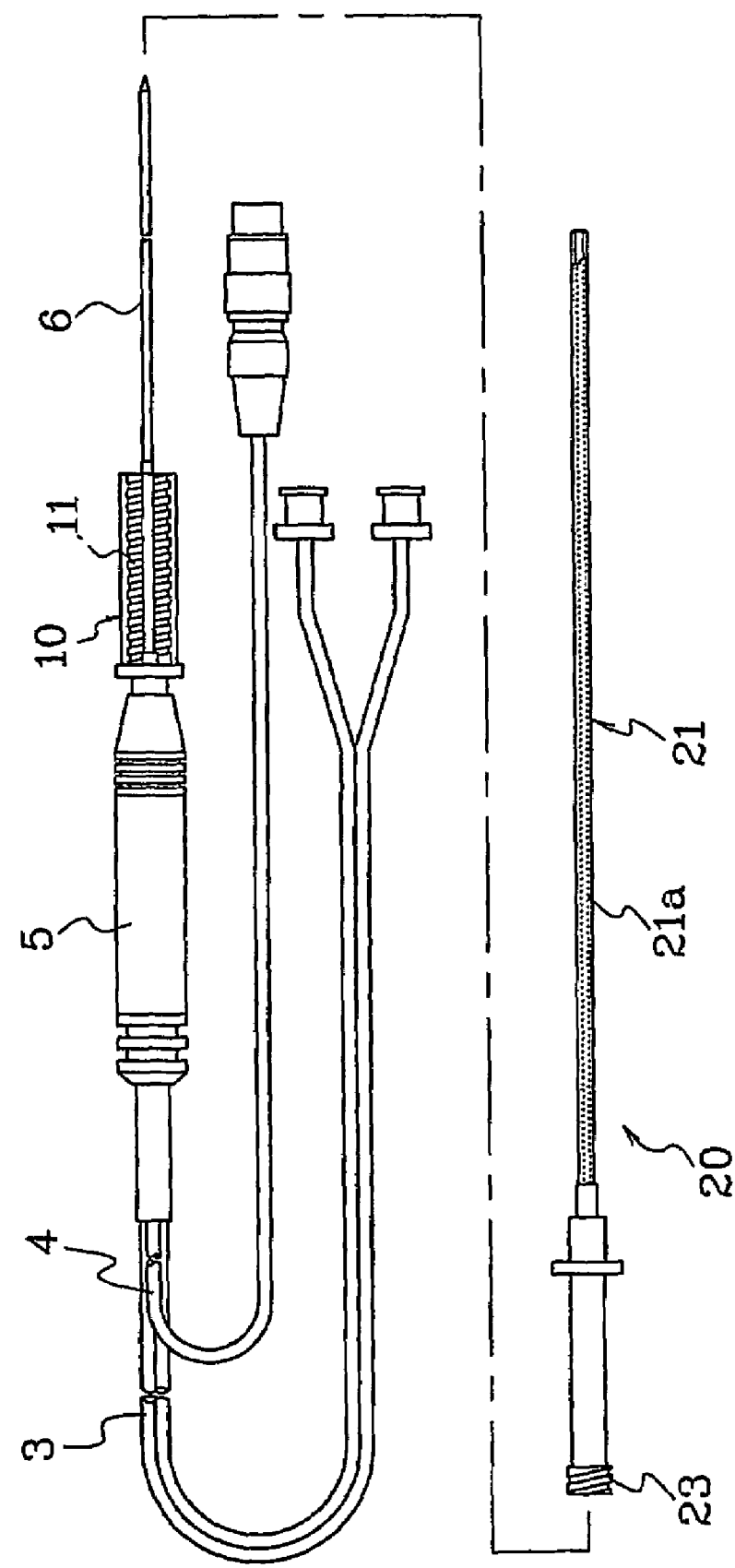
FIG. 3 is an exploded view of an electrode device for high frequency thermotherapy, according to a first embodiment of the present invention.
Figure 4:
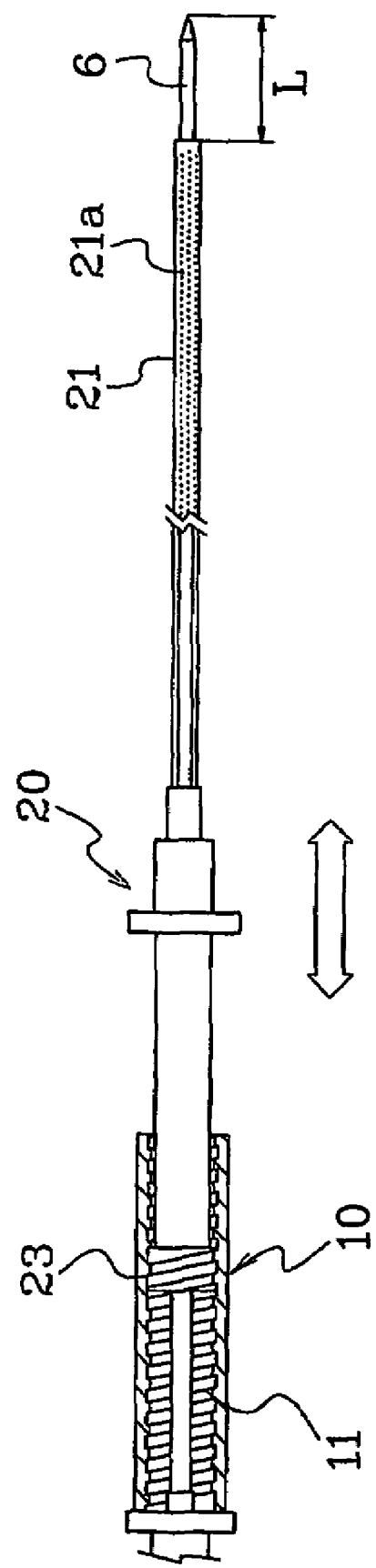
FIG. 4 is a view of assembled important parts of the electrode device of FIG. 3.

As shown in FIGS. 3 and 4, an electrode device for high frequency thermotherapy according to a first embodiment of the present invention includes a main casing 5, an electrode needle 6 which is coupled to a first end of the main casing 5, an electrode cable which is coupled to a second end of the main casing 5 to supply a high frequency wave to the electrode needle 6, and a cooling tube 3 which is coupled to the second end of the main casing 5 to circulate cooling water to or from the electrode needle 6.

The electrode device further includes a first engaging part 10 which is provided on the first end of the main casing 5. The first engaging part 10 has therein an externally threaded hole 11. The electrode device further includes a guide unit 20 which is coupled to the first engaging part 10 of the main casing 5 to be longitudinally moved relative to the electrode needle 6 while the electrode needle 6 is inserted in the guide unit 20. The guide unit 20 has at a first end thereof a guide tube 21 to receive therein the electrode needle 6 to expose a tip of the electrode needle 6 to an outside of an end of the guide tube 21, with an insulating layer 21a provided on an outer surface of the guide tube 21 to insulate the guide tube 21 from an outside of the guide tube 21. The guide unit 20 further has at a second end thereof an externally threaded part 23 to engage with the internally threaded hole 11 of the first engaging part 10. In the electrode device of the present invention, a length of a predetermined portion of the tip of the electrode needle 6, which is exposed from the end of the guide tube 21 to the outside, is varied according to a position of the guide unit 20 that is coupled to the first engaging part 10 of the main casing 5.

That is, when the externally threaded part 23 of the guide unit 20 is positioned at an outer end of the internally threaded hole 11 of the first engaging part 10 while engaging with the internally threaded hole 11 of the first engaging part 10, the end of the guide tube 21 is leveled with an end of the tip of the electrode needle 6. Thus, the tip of the electrode needle 6 is not exposed to the outside of the end of the guide tube 21. In the above state, a length of the predetermined portion of the tip of the electrode needle 6, which is exposed to the outside, is varied in proportion to a depth from the outer end of the first engaging part 10 to the position that the externally threaded part 23 of the guide unit 20 engages with the internally threaded hole 11 of the first engaging part 10.

The main casing 5 and the guide unit 20 of the electrode device of the present invention may have another structure to control the position at which the guide unit 20 is coupled to the main casing 5, in place of the threaded engagement structure, according to a modified process that falls within meets and bounds of claims of the present invention, or equivalence of such meets and bounds are therefore intended to be embraced by the claims.

The operation of the electrode device of the present invention will be described herein below. First, a conductive length L of the electrode needle 6 is controlled according to a size of a lesion of a patient body.

That is, the guide unit 20 is longitudinally moved according to the position that the externally threaded part 23 of the guide unit 20 engages with the internally threaded hole 11 of the engaging part 10 of the main casing 5. Thus, the length of the tip of the electrode needle 6, which is exposed from the end of the guide tube 21 to the outside, is controlled.

At this time, the conductive length L of the tip of the electrode needle 6, exposed from the end of the guide tube 21, is a range that high frequency wave is radiated from the tip of the electrode needle 6. Therefore, the exposed conductive length L of the tip of the electrode needle 6 is controlled according to the size of the lesion.

Thereafter, the electrode cable 4 is connected between the electrode needle 6 and a high-frequency generator which is not shown. The cooling tube 3 is connected to a cooling pump (not shown) to circulate the cooling water to or from the electrode needle 6. An electrode pad 2, which is in contact with the patient body, is connected to the high-frequency generator through an additional electrode cable.

Figure 5:
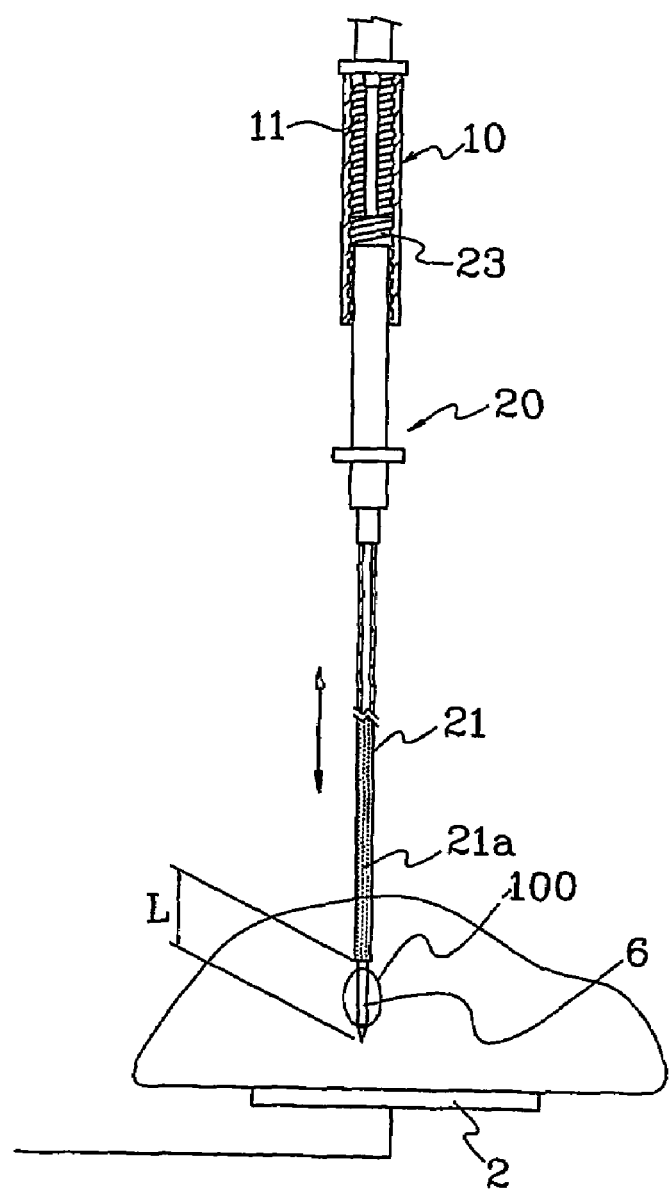
FIGS. 5 and 6 are views showing an operation of the electrode device of FIG. 3.

In the above state, a user inserts the electrode needle 6 and the guide tube 21 of the guide unit 20 into the organ of the patient body with the lesion 100 after confirming a position of the lesion 100, such that the tip of the electrode needle 6, exposed from the end of the guide tube 21, passes through the lesion 100, for example, cancer tissues. (see, FIG. 5)

Thereafter, the high frequency wave is supplied to the electrode needle 6 by the high-frequency generator. Thus, the high frequency wave is radiated from the tip of the electrode needle 6 which is exposed from the end of the guide tube 21 by the predetermined length L. Therefore, the lesion 100 is cauterized, and thus, necrotized by high frequency heat.

At this time, the high frequency wave is not radiated from a remaining part of the electrode needle 6 except for the exposed tip of the electrode needle 6, because the remaining part of the electrode needle 6 is received in the guide tube 21 with the insulating layer 21a provided on the outer surface of the guide tube 21.

Even after the guide tube 21 and the electrode needle 6 are inserted into the organ of the patient body with the lesion 100, the exposed length L of the tip of the electrode needle 6 is controlled by controlling the position of the guide tube 21. Therefore, it is possible to control the range of radiation of the high frequency wave, even after the insertion of the guide tube 21 of the electrode needle 6.

Figure 6:
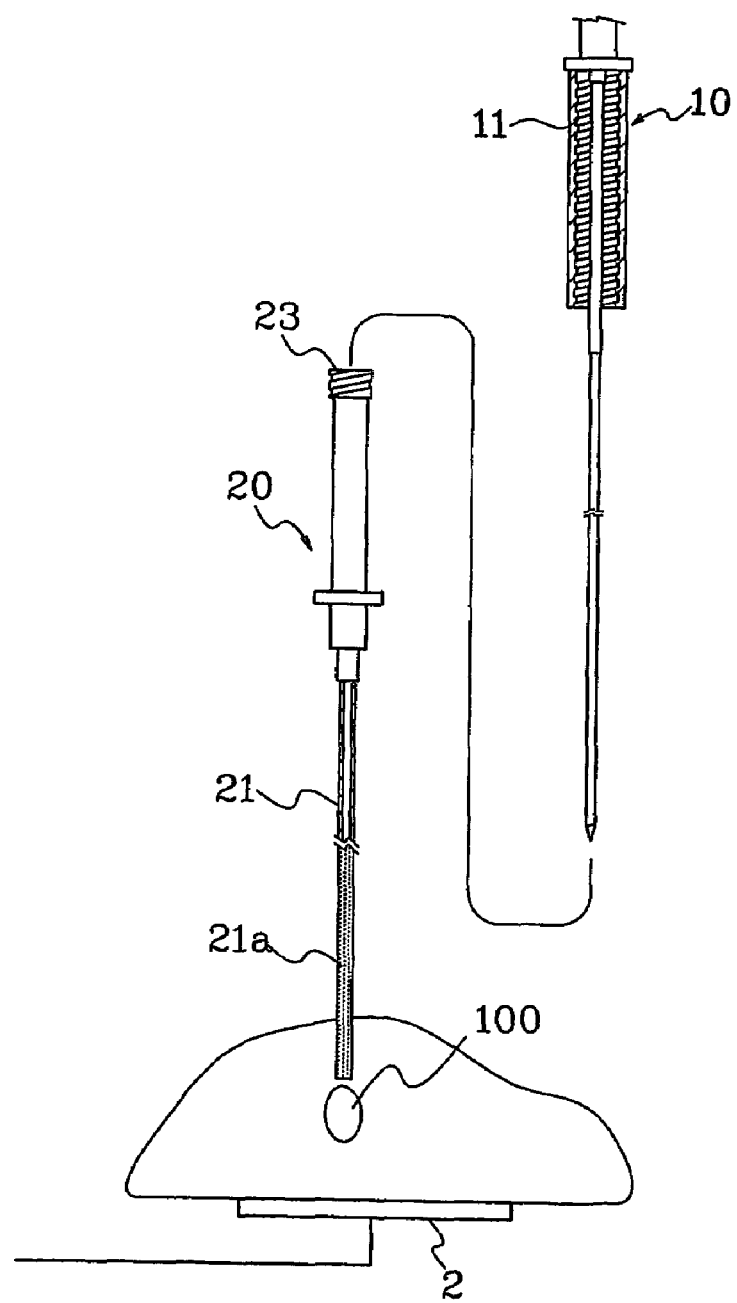

After the operation of cauterizing the lesion 100 is completed, only the electrode needle 6 is removed from the organ of the patient body with the lesion 100 while the insertion of the guide unit 20 is maintained. (see, FIG. 6) The above-mentioned maintenance of the insertion of the guide unit 20 leaves an inserting hole for repeated insertions of the electrode needle 6 to the organ of the patient body.

In case that the high frequency thermotherapy is required again after the first thermotherapy operation is executed, the electrode needle 6 is inserted to the organ of the patient body with the lesion 100 through the guide tube 21 of the guide unit 20 which was already inserted in the first thermotherapy operation.

Therefore, even when the thermotherapy operation is repeatedly executed, it is unnecessary to insert the electrode needle 6 through a new part of the organ of the patient body with the lesion 100. Thus, pain of the patient and danger caused by the insertion of the electrode needle 6 are reduced.

Figure 7:
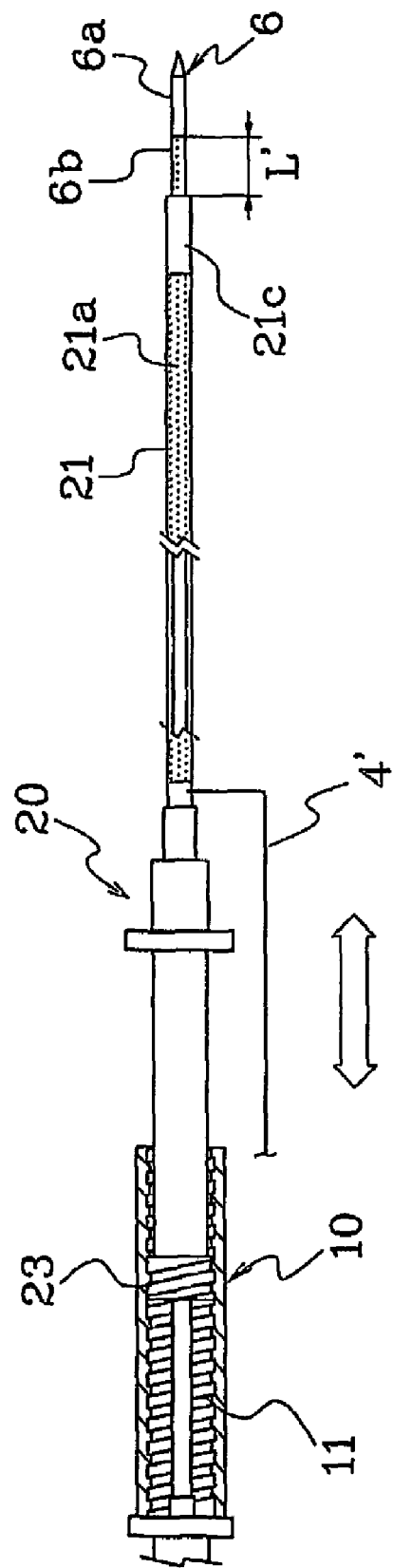
FIG. 7 is a view of assembled important parts of an electrode device for high frequency thermotherapy, according to a second embodiment of the present invention.
Figure 9A:
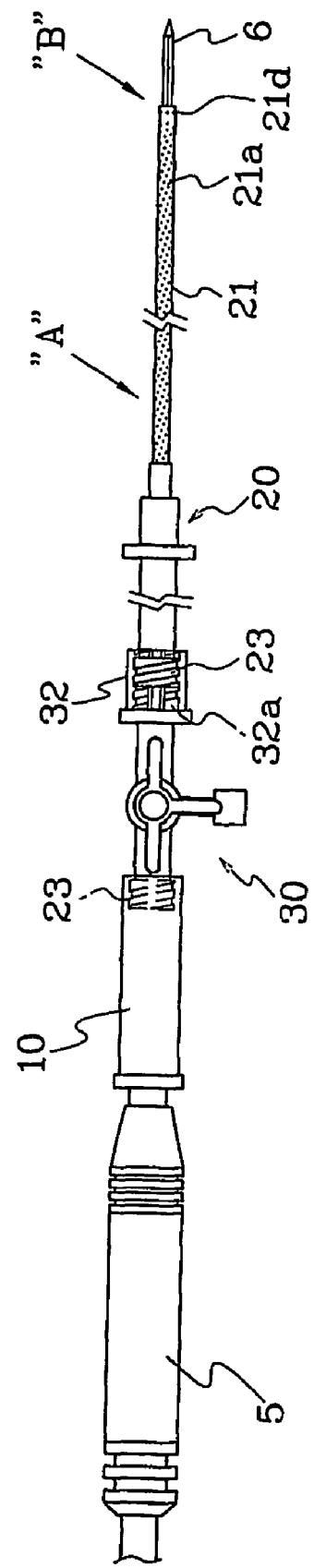
FIG. 9a is a front view of an electrode device for high frequency thermotherapy, according to a fourth embodiment of the present invention.
Figure 9B:
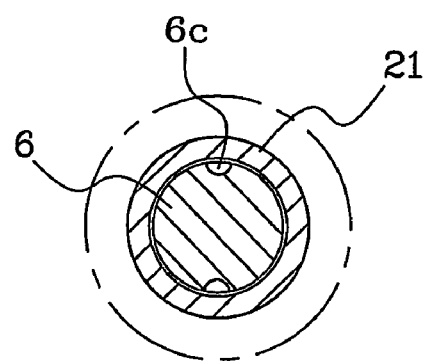
FIGS. 9b and 9c are partially enlarged sectional views of portions A and B of FIG. 9a, respectively.
Figure 9C:
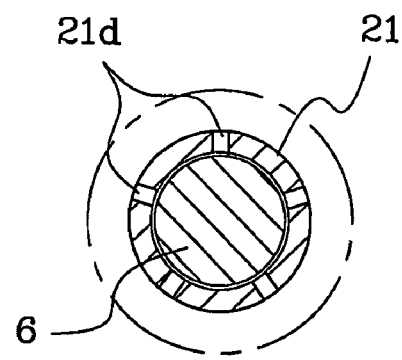

As shown in FIG. 7, in an electrode device for high frequency thermotherapy according to a second embodiment of the present invention, different from the electrode device of the first embodiment of FIGS. 3 and 4, an electrode needle 6 includes a conductive needle part 6a which is defined at a predetermined part of a tip of the electrode needle 6, and an insulating needle part 6b which is defined at a remaining part of the electrode needle 6 except for the conductive needle part 6a. A guide tube 21 of the guide unit 20 to receive the electrode needle 6 therein includes a conductive guide tube part 21c which is defined at a predetermined part of an end of the guide tube 21, and an insulating guide tube part 21a which is defined at a remaining part of the guide tube 21 except for the conductive guide tube part 21c.

Furthermore, in the electrode device according to the second embodiment, anode and cathode electrode cables 4 (see FIG. 3. the cathode electrode cables being the same as in the embodiment shown in FIG. 3) and 4' are respectively connected to the electrode needle 6 and the guide tube 21 of the guide unit 20 without the electrode pad 2 which is in contact with the patient body.

The electrode device according to the second embodiment is operated in the same manner as that described for the electrode device of the first embodiment. The electrode device of the second embodiment is preferably used in case that the lesion 100 has a relative large size, or two lesions 100 are positioned at a predetermined interval between them. That is, the high frequency wave is radiated from the conductive needle part 6a defined at a predetermined part of a tip of the electrode needle 6. Simultaneously, the high frequency wave is also radiated from the conductive guide tube part 21c which is defined at the predetermined part of the end of the guide tube 21 that is spaced apart from the conductive needle part 6a at a length L' of a predetermined part of the insulating guide tube part 6b which is exposed from the end of the guide tube 21 to the outside of the guide tube 21. Thus, the electrode device of the second embodiment simultaneously cauterizes the two lesions 100, spaced apart from each other at the predetermined interval, using high frequency heat.

At this time, the length L' between the conductive needle part 6a of the electrode needle 6' and the conductive guide tube part 21c of the guide tube 21 is varied according to the position that the guide unit 20 is coupled to the engaging part 10 of the main casing 5.

As described above, because the operation of cauterizing the lesion 100 is executed at two parts spaced apart from each other to increase the range of cauterizing the lesion 100, the electrode device of the second embodiment is preferably used in the thermotherapy operation of cauterizing the large lesion 100.

As shown in FIGS. 8, 9a, 9b and 9c, each of electrode devices for high frequency thermotherapy according to third and fourth embodiments of the present invention includes a three-way valve 30 to insert therein the electrode needle 6. The three-way valve 30 has a second engaging part 32 which is provided on a first end of the three-way valve 30, with an internally threaded hole 32a provided in the second engaging part 32. The three-way valve 30 further has an externally threaded part 31 which is provided on a second end of the three-way valve 30. The externally threaded part 31 of the three-way valve 30 engages with an internally threaded hole 32a which is provided in the first engaging part 10 of the main casing 5. The internally threaded hole 32a of the second engaging part 32 engages with the externally threaded part 23 which is provided on the second end of the guide unit 20. Thus, a liquid medicine or water is supplied from the three-way valve 30 to the lesion 100 of the patient body through a path defined between the electrode needle 6 and the guide tube 21.

At this time, the liquid medicine is a material, such as saline water, that increases the range of cauterizing the lesion 100 of the patient body using the high frequency wave.

The electrode device according to each of the third and fourth embodiments further includes at least one longitudinal groove 6c which is provided along the electrode needle 6 to smoothly supply the water or the liquid medicine to the lesion 100.

The electrode device according to the fourth embodiment further includes a plurality of discharging holes 21d which are provided around a circumferential outer surface of the end of the guide tube 21 of the guide unit 20.

In the electrode device of each of the third and fourth embodiments, the three-way valve 30 is coupled to the main casing 5, and the guide unit 20 is thereafter coupled to the three-way valve 30. Thereafter, the electrode needle 6 is inserted to the organ of the patient body with the lesion 100, thus cauterizing the lesion 100 by high frequency heat.

The liquid medicine or the water, supplied to the three-way valve 30, is injected from the end of the guide tube 21 to the lesion 100 through the path defined between the electrode needle 6 and the guide tube 21.

Due to the liquid medicine or the water injected to the lesion 100, the high frequency wave is more widely radiated to the lesion 100. Thus, the range of the lesion 100, cauterized by the high frequency heat, is increased.

In the electrode device according to the fourth embodiment, the liquid medicine or the water is more evenly injected to the lesion 100 through the plurality of discharging holes 21d which are provided around the circumferential outer surface of the end of the guide tube 21. Therefore, the high frequency wave is more evenly and widely radiated to the lesion 100, thus effectively cauterizing the lesion 100.

As described above, the electrode device for the high frequency thermotherapy of the present invention simply increases the range of the lesion 100, cauterized by the high frequency heat, during the operation of cauterizing the lesion 100. Thus, the number of insertions of the electrode needle 6 on the patient body is reduced. Therefore, the electrode device of the present invention reduces the pain of the patient and simplifies the thermotherapy operation.

In the electrode device according to each of the third and fourth embodiments, the three-way valve 30 may be coupled to a separate valve while being provided between the engaging part 10 and the guide unit 20. The three-way valve 30 must have a structure capable of supplying the liquid medicine or the water to the lesion 100 through the path defined between the electrode needle 6 and the guide tube 21.

INDUSTRIAL APPLICABILITY

As described above, the present invention provides an electrode device for high frequency thermotherapy, which has a structure capable of controlling a length of a predetermined part of a tip of an electrode needle, exposed from an end of a guide unit to the outside, according to a size of a lesion, thus efficiently executing a thermotherapy operation, and being more convenient for a user. Furthermore, the electrode device of the present invention has a guide tube inserted along with the electrode needle to the lesion of the patient body. Thus, only the electrode needle is inserted to or removed from the lesion through the inserted guide tube while the insertion of the guide tube is maintained, even when the thermotherapy operation is repeatedly executed, or the existing electrode needle is changed with another one. Therefore, the electrode device of the present invention reduces pain of the patient and harm caused by the repeated thermotherapy operations.

Furthermore, the electrode device for the high frequency thermotherapy of the present invention has a structure capable of supplying water or liquid medicine to the lesion to increase a range of radiation of a high frequency wave, thus increasing a range of cauterizing the lesion. Therefore, the number of operations for inserting the electrode needle to the lesion of the patient body is reduced, even when the lesion has a wide size.

The invention claimed is:

1. An electrode device for high frequency thermotherapy, comprising a main casing; an electrode needle coupled to a first end of the main casing; an electrode cable coupled to a second end of the main casing to supply a high frequency wave to the electrode needle; a cooling tube coupled to the second end of the main casing to circulate cooling water to or from the electrode needle, and further comprising:
   a first engaging part provided on the first end of the main casing; and
   a guide unit coupled to the first engaging part of the main casing to be longitudinally moved relative to the electrode needle while the electrode needle is inserted in the guide unit, the guide unit comprising:
      a guide tube to receive therein the electrode needle to expose a tip of the electrode needle to an outside of an end of the guide tube, with an insulating layer provided on an outer surface of the guide tube to insulate the guide tube from an outside of the guide tube, wherein
   the electrode needle comprises a conductive needle part defined at a predetermined part of the tip of the electrode needle and an insulating needle part defined at a remaining part of the electrode needle except for the conductive needle part, and
   the guide tube of the guide unit to receive the electrode needle therein comprises a conductive guide tube part defined at a predetermined part of the end of the guide tube and an insulating guide tube part defined at a remaining part of the guide tube except for the conductive guide tube part, and
   a length of the tip of the electrode needle, which is exposed from the end of the guide tube to the outside, is varied according to a position that the guide unit is coupled to the first engaging part of the main casing.

2. The electrode device according to claim 1, further comprising:
   a three-way valve to insert therein the electrode needle, the three-way valve comprising:
      a second engaging part provided on a first end of the three-way valve, with an internally threaded hole provided in the second engaging part; and
      an externally threaded part provided on a second end of the three-way valve,
   wherein the externally threaded part of the three-way valve engages with an internally threaded hole provided in the first engaging part of the main casing, and the internally threaded hole of the second engaging part engages with an externally threaded part provided on the second end of the guide unit, so that a liquid medicine or water is supplied from the three-way valve to a desired part of a patient body through a path defined between the electrode needle and guide tube.

3. The electrode device according to claim 2, further comprising:
   at least one longitudinal groove provided along the electrode needle.

4. The electrode device according to claim 2, further comprising:
   a plurality of discharging holes provided around a circumferential outer surface of the end of the guide tube of the guide unit.

* * * * *